US008865194B1

(12) United States Patent
Gans et al.

(10) Patent No.: US 8,865,194 B1
(45) Date of Patent: Oct. 21, 2014

(54) REDUCING TACKINESS AND GREASINESS OF PETROLATUM-LIKE MATERIALS

(75) Inventors: Eugene H. Gans, Westport, CT (US); Hans R. Suess, Dulliken (CH)

(73) Assignee: Theraplex Company, LLC, Memphis, TN (US)

( * ) Notice: Subject to any disclaimer, the term of this patent is extended or adjusted under 35 U.S.C. 154(b) by 901 days.

(21) Appl. No.: 12/339,411

(22) Filed: Dec. 19, 2008

Related U.S. Application Data

(60) Provisional application No. 61/015,389, filed on Dec. 20, 2007.

(51) Int. Cl.
| | | |
|---|---|---|
| *A61K 8/19* | (2006.01) | |
| *A61K 8/27* | (2006.01) | |
| *A61K 8/31* | (2006.01) | |
| *A61K 8/55* | (2006.01) | |
| *A61K 8/58* | (2006.01) | |
| *A61K 8/92* | (2006.01) | |
| *A61Q 19/00* | (2006.01) | |
| *A61K 8/02* | (2006.01) | |

(52) U.S. Cl.
CPC ... *A61K 8/19* (2013.01); *A61K 8/27* (2013.01); *A61K 8/585* (2013.01); *A61K 8/31* (2013.01); *A61Q 19/00* (2013.01); *A61K 8/92* (2013.01); *A61K 8/553* (2013.01); *A61K 8/0216* (2013.01)
USPC ........................................ 424/401; 424/78.03

(58) Field of Classification Search
None
See application file for complete search history.

(56) References Cited

U.S. PATENT DOCUMENTS

| | | | |
|---|---|---|---|
| 4,009,254 A | | 2/1977 | Renold |
| 4,355,046 A | * | 10/1982 | Suess ............................ 514/772 |
| 4,671,955 A | | 6/1987 | Palinczar |
| 4,699,780 A | | 10/1987 | Jennings et al. |
| 4,760,096 A | * | 7/1988 | Sakai et al. ................... 514/786 |
| 4,944,937 A | | 7/1990 | McCall |
| 4,960,592 A | | 10/1990 | Hagen et al. |
| 5,266,321 A | | 11/1993 | Shukuzaki et al. |
| 5,310,556 A | | 5/1994 | Ziegler |
| 5,552,147 A | | 9/1996 | Znaiden et al. |
| 5,552,148 A | | 9/1996 | Znaiden et al. |
| 5,660,839 A | | 8/1997 | Allec et al. |
| 5,690,918 A | | 11/1997 | Jacks et al. |
| 5,725,844 A | | 3/1998 | Gers-Barlag et al. |
| 5,733,531 A | | 3/1998 | Mitchnick et al. |
| 5,744,146 A | | 4/1998 | Peters et al. |
| 5,849,275 A | | 12/1998 | Calello et al. |
| 5,871,760 A | | 2/1999 | Doughty et al. |
| 5,939,083 A | | 8/1999 | Allec et al. |
| 5,948,417 A | | 9/1999 | Mori |
| 5,968,495 A | | 10/1999 | Bolich, Jr. et al. |
| 6,017,552 A | | 1/2000 | Mori |
| 6,036,945 A | | 3/2000 | Deblasi et al. |
| 6,197,282 B1 | | 3/2001 | Oshima et al. |
| 6,200,580 B1 | | 3/2001 | Horino et al. |
| 6,290,940 B1 | | 9/2001 | Meyers et al. |
| 6,387,405 B1 | | 5/2002 | Shah et al. |
| 6,423,326 B1 | | 7/2002 | Shapiro |
| 6,645,502 B2 | | 11/2003 | Sandewicz et al. |
| 2005/0031655 A1 | | 2/2005 | Karpov |
| 2007/0207102 A1 | * | 9/2007 | Student et al. .................. 424/63 |

FOREIGN PATENT DOCUMENTS

| | | |
|---|---|---|
| DE | 19939836 A1 | 2/2001 |
| EP | 1054660 | 2/1999 |
| EP | 1055410 | 11/2000 |
| EP | 1055414 | 11/2000 |
| EP | 1055418 | 11/2000 |

OTHER PUBLICATIONS

Gregor B. E. Jemec and Hans Christian Wulf, "The greasiness of moisturizers: A methodological study", May/Jun. 1998, pp. 175-181, Journal of Cosmetic Science, 49.
Chemical Abstracts, 148: 479855n, titled "Dermatological Formulations" Published Oct. 20, 2006.
Fiedler Encyclopedia of Excipients; Author Eva-Marie Hoepfner et al. Title "Lecithin" pp. 960-962. (2002).
Bulletin de la Societe de Chimine Biologuque, vol. 32, Author M. Faure & J. Legault-Demare, pp. 509-512, published in Paris, France in 1950.

* cited by examiner

*Primary Examiner* — Daniel Sullivan
*Assistant Examiner* — Barbara Frazier
(74) *Attorney, Agent, or Firm* — Pearne & Gordon LLP

(57) ABSTRACT

Skin-protecting ointment compositions are disclosed that include a greasy material, a safe and minimally absorbed solid, and optionally, a phospholipid composition, and that exhibit reduced greasiness and tackiness relative to an otherwise identical composition lacking the safe and minimally absorbed solid and the optional phospholipid composition. Also disclosed are methods of making such skin-protecting ointment compositions. In one embodiment, the skin-protecting ointment composition comprises a safe and minimally absorbed solid, a lipid thickener, an ointment-like material, a volatile oil, and optionally a phospholipid composition. In another embodiment, the method of making the skin-protecting ointment composition comprises combining a greasy material and a safe and minimally absorbed solid, mixing the greasy material and the safe and minimally absorbed solid, optionally adding a phospholipid composition dissolved in a volatile oil, and cooling the combined composition to impede oxidation of the phospholipid composition.

20 Claims, No Drawings

REDUCING TACKINESS AND GREASINESS OF PETROLATUM-LIKE MATERIALS

CROSS-REFERENCE TO RELATED APPLICATIONS

This application claims the benefit of U.S. Provisional Application No. 61/015,389, filed Dec. 20, 2007, the entire disclosure of which is hereby incorporated herein by reference.

FIELD OF THE INVENTION

The present invention relates to a skin-protecting ointment composition that has a high content of a greasy material but that exhibits relatively low greasiness and tackiness, and methods of use thereof.

BACKGROUND OF THE INVENTION

The problem of dry, damaged skin is well known. The distant ancestors of the human species, upon leaving the ocean, initially adapted to life in a relatively more desiccating terrestrial environment by developing hair-bearing pelts on their bodies. Since then, as evolution forced the erect walk, our ancestors have gradually lost their pelts, developing instead sebum, which makes hair repellent to water and provides hair with tocopherol as an antioxidant. With the industrial revolution, soap and synthetic surfactants have been created and used for washing the skin, with the result that the sebum layer is removed and the skin is left relatively unprotected. For example, the most exposed part of the body now typically is the dorsum of the hands, since people typically wash their hands several times each day, thus eliminating protection by sebum. Moreover, since life expectancy has been increasing, aged people have been showing increased skin damage caused mainly by UV radiation. In addition, dermal fiber proteins and extracellular matrices are crucial for retention of the protective properties of skin. The alteration of the proteins and matrices during actinic aging decreases the resilience of the skin and all other connective tissues, causing changes such as wrinkles. With age, the production of epidermal lipids decreases, resulting in increased trans-epidermal water loss and more dry skin. Thus, the main environmental threats to the skin are penetration of stripping agents such as synthetic detergents, UV radiation, and increased epidermal water loss, especially when the surrounding air is dry and/or cold.

Ideally, a skin-protecting ointment composition should help to solve these problems. Furthermore, the tolerability and sensorial properties of an ointment composition's components must be of a high order, since dry skin is a chronic problem for many people, essentially necessitating application for life.

One approach to solving the problem of dry, damaged skin has been use and application of petrolatum as a major component of skin-protecting ointment compositions. Petrolatum has very desirable characteristics in terms of being long-lasting and water repellant, and, indeed, petrolatum is the standard reference substance for skin protection. However, petrolatum's greasiness and tacky sensory properties are poorly acceptable. An example of greasiness is when a material, often a wholly or partially water immiscible lipid, sticks to the substrate, e.g. skin, with which it is in contact. One problem with a greasy material is that it remains poorly or incompletely absorbed and thus leaves a residue that imparts a tacky, often "lipoidal-like," sensation upon touch. The sensation is often also described as "greasy." A related problem with greasy materials is that they readily transfer to substrates that they contact, often contaminating and staining the substrates. Common greasy materials include many fractions of petroleum and related hydrocarbons such as mineral oils, petrolatum, and hydrocarbon/mineral waxes, such as ozokerite; animal fats, such as the lanolins; plant lipids; and synthetic materials, such as many types of silicones, hydrocarbons, esters, ethers, and other structures.

One approach to reduce the greasiness of greasy materials has involved isolation of the materials from substrates, either by encapsulation or by incorporation into the internal, discontinuous phases of emulsions, such as in oil-in-water emulsions. Unfortunately, the amount of greasy materials must be reduced to much less than 50% of their normal amounts in ointment compositions. Since the greasy materials are inside capsules or are in the internal phase of emulsions, the materials do not directly contact the skin or other substrate to which they are applied. Rather, the greasy materials contact the skin or other substrate in a discontinuous mode, thus reducing total contact area and total concentration of greasy materials that can be applied.

Another approach has involved adsorption or absorption of greasy materials onto or into solid components, such as silicates. This approach can be effective. Unfortunately, though, a high amount of adsorbent or absorbent is often required, representing for example 25% to 100% of the weight of the greasy material. The result, again, is a significant reduction in the availability or bioavailability of the greasy material to the substrate.

Accordingly, one object of the present invention is to improve the sensory properties of greasy materials, such as petrolatum, in skin-protecting ointment compositions, since sensory properties are important to acceptance and continued use of the compositions. Another object of the present invention is to accomplish the improvement by adding only a minimal number of safe, well tolerated agents. And another object of the present invention is to enhance inherent UV-protecting properties of greasy materials, again such as petrolatum, in skin-protecting ointment compositions.

BRIEF SUMMARY OF THE INVENTION

The following presents a simplified summary of the invention in order to provide a basic understanding of some example aspects of the invention. This summary is not an extensive overview of the invention. Moreover, this summary is not intended to identify critical elements of the invention nor delineate the scope of the invention. The sole purpose of the summary is to present some concepts of the invention in simplified form as a prelude to the more detailed description that is presented later.

In accordance with the present invention, it has been realized that an unexpected and gratifying reduction in the greasiness and tackiness of greasy materials can be accomplished, without the creation of encapsulates or emulsions and without the use of large quantities of adsorbents or absorbents, based on the use of a relatively small quantity of a safe and minimally absorbed solid, such as boron nitride and/or zinc oxide, optionally and preferably in combination with a relatively small amount of a phospholipid composition, such as a non-deoiled soy lecithin. Moreover, it has been realized that a skin-protecting ointment composition comprising a greasy material, a safe and minimally absorbed solid, and optionally and preferably a phospholipid composition provides an unexpected and gratifying improvement of skin sensation, corresponding to a relative reduction in greasiness and tackiness, with no apparent sacrifice regarding valuable skin-protection properties, such as long-lasting water repellency, reduction in epidermal water loss, resistance to removal by detergents, and contribution to protection against UV radiation. In addition, it has been realized that the skin-protecting ointment composition enhances the modest but useful inherent UV-protecting property of certain greasy materials, such as petrolatum, that may be included therein. Furthermore, it has been realized that a method of making the skin-protecting ointment composition comprises the step of combining a greasy material, a safe and minimally absorbed solid, and optionally and preferably a phospholipid composition. Further still, it has been realized that a method of reducing the greasiness and tackiness of the skin-protecting ointment comprises the step of combining a greasy material, a safe and minimally absorbed solid, and a non-deoiled phospholipid composition that is dissolved in a volatile oil. Further still, it has been realized that a method of use of the skin-protecting ointment composition comprises application of the composition to skin.

In accordance with one aspect of the present invention, the skin-protecting ointment composition comprises: a safe and minimally absorbed solid at 0.1 to 20 w/w %; a lipid thickener at 1 to 40 w/w %; an ointment-like material at 25 to 65 w/w %; and a volatile oil at 10 to 50 w/w %, said ointment composition exhibiting reduced greasiness and tackiness relative to an otherwise identical composition lacking the safe and minimally absorbed solid.

In accordance with another aspect of the present invention, the skin-protecting ointment composition comprises boron nitride at 0.5 to 15 w/w % and a greasy material at 40 to 99 w/w %, said ointment composition exhibiting reduced greasiness and tackiness relative to an otherwise identical composition lacking the boron nitride.

In accordance with another aspect of the present invention, the skin-protecting ointment composition comprises a safe and minimally absorbed solid at 0.1 to 20 w/w %; a phospholipid composition at 0.5 to 10 w/w %; and a greasy material at 40 to 99 w/w %, said ointment composition exhibiting reduced greasiness and tackiness relative to an otherwise identical composition lacking the safe and minimally absorbed solid and the phospholipid composition; said safe and minimally absorbed solid being selected from the group consisting of boron nitride, boron nitride in a crystalline form, boron nitride in the form of micronized or microcrystallized alpha hexagonal crystals, zinc oxide, titanium dioxide, polytetrafluoroethylene, talcum, and pigments; said phospholipid composition being selected from the group consisting of a phospholipid, a refined phospholipid, a natural phospholipid, a non-deoiled phospholipid, a lecithin, a refined lecithin, a natural lecithin, a non-deoiled lecithin, a soy lecithin, a refined soy lecithin, a natural soy lecithin, a non-deoiled soy lecithin, or a modified lecithin; said greasy material comprising a lipid thickener, an ointment-like material, and a volatile oil; said lipid thickener being selected from the group consisting of wax, ozokerite wax, beeswax, natural and synthetic waxes, and lipid miscible thickeners; said ointment-like material being selected from the group consisting of petrolatum, lanolin, natural lipid, synthetic lipid, high molecular weight glyceride, and polyethylene glycol; and said volatile oil being selected from the group consisting of isohexadecane, cyclomethicone, cyclomethicone D4, isododecane, and safe, volatile liquid oil.

In accordance with another aspect of the present invention, the method of making the skin-protecting ointment composition comprises the steps of combining a greasy material and a safe and minimally absorbed solid, mixing the greasy material and the safe and minimally absorbed solid, optionally adding a phospholipid composition dissolved in a volatile oil, and cooling the resulting composition to impede oxidation of the phospholipid composition; said ointment composition exhibiting reduced greasiness and tackiness relative to an otherwise identical composition lacking the safe and minimally absorbed solid and the optionally added phospholipid composition.

In accordance with another aspect of the present invention, the method of reducing the greasiness and tackiness of the skin-protecting ointment composition comprises the step of combining a greasy material, a safe and minimally absorbed solid, and a non-deoiled phospholipid composition that is dissolved in a volatile oil to form the skin-protecting ointment composition, said ointment composition exhibiting reduced greasiness and tackiness relative to an otherwise identical composition lacking the safe and minimally absorbed solid and the phospholipid composition.

In accordance with another aspect of the present invention, the method of protecting skin comprises the steps of applying the skin-protecting ointment composition to skin and rubbing the composition into the skin.

DESCRIPTION OF EXAMPLE EMBODIMENTS

Example embodiments that incorporate one or more aspects of the present invention are described. These examples are not intended to be a limitation on the present invention. For example, one or more aspects of the present invention can be utilized in other embodiments and even other types of compositions and methods. Moreover, certain terminology is used herein for convenience only and is not to be taken as a limitation on the present invention.

As used herein, when a range such as 5-25, 5 to 25, or between 5 and 25 is given, this means preferably at least 5 and, separately and independently, preferably not more than 25. Also as used herein, unless otherwise stated, a weight/weight % (w/w %) refers to weight of a material in a weight of a composition in an anhydrous form. By way of example, a composition with a phospholipid at 50 w/w % includes the phospholipid at a weight equal to the sum of the weights of all of the remaining substances of the anhydrous formulation.

As used herein and in the claims, the term "ointment" refers to a viscous or semisolid substance used on the skin as a cosmetic, emollient, or medicament. Reduction of the greasiness of an ointment is relatively challenging in comparison, for example, to reduction of the greasiness of a cosmetic stick. This is because ointments typically include compounds that are relatively more greasy and less solid, and include relatively more of these compounds, in comparison to sticks. Thus, application of a stick tends to result in a more solid deposit on the surface of application, whereas application of an ointment tends to result in a residue on the surface, with decreasing solidities of solid components in ointments tending to result in relatively softer and more easily spreadable compositions or structures, though with increased greasiness.

As used herein and in the claims, the term "safe and minimally absorbed solids" refers to micro- and nano-particulates that are safe and well tolerated upon application to human skin (i.e. have been shown, in use, to be safe) and that are absorbed by the body systems to no more than a minimal extent when used in accordance with the present invention. A safe and minimally absorbed solid preferably corresponds to boron nitride, boron nitride in a crystalline form, boron nitride in the form of micronized or microcrystallized alpha hexagonal crystals zinc oxide, titanium dioxide, polytetrafluoroethylene (preferably without the carcinogenic compound perfluorooctanoic acid), talcum, and other pigments, and more preferably corresponds to boron nitride, boron nitride in a crystalline form, boron nitride in the form of micronized or microcrystallized alpha hexagonal crystals, and zinc oxide.

Boron nitride may be obtained in various forms, including various crystalline forms. A preferred form of boron nitride is micronized or microcrystallized alpha hexagonal crystals with a size distribution that favors soft, impalpable feeling on the skin. One such useful particle size distribution is 1 to 20 microns with a molecular-weight-distribution peak at approximately 5 microns. Other crystalline forms of boron nitride include a beta form and a gamma form.

Zinc oxide may be obtained in various forms, including zinc oxide USP and micronized zinc oxide. The zinc oxide preferably should be one of a lower microsize, for example one obtained by an American process whereby zinc vapor is oxidized, and should be one for which the tendency of the microsize particles to aggregate has been suppressed.

Certain safe and minimally absorbed solids provide additional benefits. For example, zinc oxide and titanium dioxide also provide UV-protective and bactericidal effects.

As used herein and in the claims, the term "phospholipid composition" refers to a composition including a phospholipid in a concentration of at least 50 w/w %, optionally in combination with a triglyceride, a fatty acid, and/or a carbohydrate. A phospholipid composition preferably comprises a phospholipid, a refined phospholipid, a natural phospholipid, a non-deoiled phospholipid, a lecithin, a refined lecithin, a natural lecithin, a non-deoiled lecithin, a soy lecithin, a refined soy lecithin, a natural soy lecithin, a non-deoiled soy lecithin, and/or a modified lecithin, and more preferably comprises a natural lecithin, a non-deoiled lecithin, a natural soy lecithin, and/or a non-deoiled soy lecithin. A non-deoiled phospholipid composition preferably comprises a natural phospholipid, a non-deoiled phospholipid, a natural lecithin, a non-deoiled lecithin, a natural soy lecithin, and/or a non-deoiled soy lecithin. As used herein and in the claims, the term "phospholipid" comprises, for example, phosphatidylcholine, phosphatidylethanolamine, and/or phosphatidylinositol. As used herein and in the claims, the term "lecithin" refers to one or more of a phospholipid, optionally in combination with a triglyceride, a fatty acid, and/or a carbohydrate. As used herein and in the claims, a "refined" phospholipid, lecithin, or soy lecithin refers to a phospholipid, lecithin, or soy lecithin, respectively, from which natural oils have been removed. As used herein and in the claims, a "natural" or "non-deoiled" phospholipid, lecithin, or soy lecithin is a phospholipid, lecithin, or soy lecithin, respectively, from which natural oils have not been removed.

As used herein and in the claims, the term "greasy material" comprises a lipid thickener, an ointment-like material, and/or a volatile oil, for example alone or in various combinations. More particularly, greasy material includes petrolatum and/or a combination of petrolatum and wax. As used herein and in the claims, the term "lipid thickener" comprises wax, ozokerite wax (i.e. ozokerite), beeswax, other natural and synthetic waxes, and/or lipid miscible thickener. As used herein and in the claims, the term "ointment-like material" comprises petrolatum, lanolin, and/or natural and synthetic lipids, including high molecular weight glycerides and polyethylene glycols and the like. As used herein and in the claims, "volatile oil" includes isohexadecane, cyclomethicone, cyclomethicone D4, isododecane, and/or other safe, volatile liquid oils, for example alone or in various combinations. Various comparatively thin to thick grades of lipid thickener, such as ozokerite, and ointment-like material, such as petrolatum, are available. Thus, the skin-protecting ointment in accordance with the present invention can be adjusted to a desired thinness/thickness based on the grades and concentrations of lipid thickener and ointment-like material. Other lipoidal agents can also be used in addition to, or in place of, petrolatum and/or ozokerite, including gelled hydrocarbons, and waxes such as beeswax, candilla wax, polyethylene glycol waxes, and the like.

Compositions in accordance with the present invention reduce the greasiness and tackiness of various greasy materials, and more particularly of ointment-like materials.

The volatile oil, such as isohexadecane, cyclomethicone, cyclomethicone D4, isododecane, or other safe, volatile liquid oil, allows the formulation to be spread easily on the skin and other substrates and to contact the cracks, fissures, and other poorly accessible crevices in the skin or other substrates. A theory of the present invention is that the enhancement of the spreading contributes to the reduction in greasiness and tackiness. Moreover, a theory of the present invention is that the volatilization also helps to anchor the otherwise greasy material present in the composition to skin or other substrate, further enhancing the ability of the ointment composition to protect the skin or other substrate from environmental or other insult.

The amount of volatile oil can be varied. For example, a reduction in the relative amount of the volatile isohexadecane or cyclomethicone will result in a composition that leaves more product on the surface of the skin (i.e. a thicker, heavier residue), and likewise an increase in the relative amount will result in a composition that leaves less product on the surface of the skin (i.e. a thinner, lighter residue).

Compositions in accordance with the present invention can also incorporate a wide range of lipophilic, amphiphilic, and hydrophilic dermatological agents, including sunscreens, sun-blocks, anti-inflammatory agents, anti-infective agents, cosmetics, anti-viral agents, protectants, enzyme adjuvants, stimulators and inhibitors, and the like. Additional optional ingredients of the compositions include the following: a modified lecithin at 0.1 to 20 w/w %, preferably at 1 to 10 w/w %; and/or cosmetic components conventionally or normally used to adjust viscosity, spreadability, fluidity, odor, and/or color, at weight percentages that are conventional and well known in the art.

Various factors affect the degree of greasiness, lack of greasiness, and time required to reduce or eliminate tackiness, upon application of a skin-protecting ointment composition in accordance with the present invention. For example, increasing amounts of the ointment composition as applied to skin, decreasing environmental temperature, and increasing environmental humidity result in higher degrees of greasiness and longer times required to reduce or eliminate tackiness. In contrast, application of a constant amount of the composition to increasingly large areas of skin and greater degrees and extents to which the composition is rubbed in to the skin normally results in lower degrees of greasiness and shorter times required to reduce or eliminate tackiness.

Compositions in accordance with the present invention may be manufactured as follows: Melt together an ointment-like material, e.g. petrolatum, and a lipid thickener, e.g. ozokerite, for example by heating to 75° C. and stirring. Add a safe and minimally absorbed solid, e.g. zinc oxide and/or boron nitride. Stir well. Optionally add a phospholipid composition, e.g. soy lecithin, dissolved in a volatile oil, e.g. isohexadecane, the solution being at 20° to 23° C. or in other words at or about room temperature, just prior to addition. Then cool the resulting composition as quickly as possible to 30° C. to impede oxidation of the phospholipid composition.

Compositions in accordance with the present invention may be used by applying the composition to the skin and then rubbing the composition into the skin until the composition is reasonably absorbed, without excessive rubbing.

One unexpected result regarding the skin-protecting ointment compositions in accordance with the present invention is their long-lasting durability on the skin and protection of the skin. For example, after applying various skin-protecting ointments in accordance with the present invention, and allowing the volatile isohexadecane or cyclomethicone to evaporate, numerous unexpected results were observed. First, the agreeable skin sensation or "skin feel" increased further. Second, water resistance continued, as noted by running water over the treated skin both minutes after, and several hours after, application, and observing that in both cases the water beads up, thus indicating that the water-protecting, lipid film is still present. Third, resistance to removal of the composition by rubbing alcohol continued. Specifically, protection against the skin drying and against the irritating effect of rubbing alcohol was observed, as noted by applying a skin-protecting composition in accordance with the present invention, waiting several minutes to allow evaporation of the volatile oil of the composition, wiping the skin with rubbing alcohol (e.g. rubbing alcohol used for disinfecting skin), and then letting water run on the skin, and observing that the water beads up, thus again indicating that the water-protecting, lipid film is still present. This effect is beneficial to medical personnel and patients who must use rubbing alcohol multiple times and on a regular basis during the day. Fourth, resistance to removal by detergents was observed. And fifth, a reduction in epidermal water loss was observed.

Another unexpected result is the degree to which improved skin sensation, increased adhesion to skin, and reduced greasiness and tackiness were achieved based on the combination of a phospholipid composition, particularly a lecithin, and more particularly a non-deoiled lecithin, with a skin-protecting ointment composition in accordance with the present invention and including zinc oxide (pharmaceutical grade). This was unexpected at least in part because preparations that contain phospholipids for forming emulsions have been disclosed for preventing adhesion. Moreover, unexpectedly, the phenomenon was much more pronounced based on use of a non-deoiled lecithin in comparison to use of a refined lecithin. Thus, a method of making a skin-protecting composition, comprising combining a greasy material, a safe and minimally absorbed solid, and a phospholipid composition, wherein the phospholipid composition includes a natural or non-deoiled phospholipid, e.g. natural lecithin, non-deoiled lecithin, natural soy lecithin, or non-deoiled soy lecithin, will yield a composition that exhibits reduced greasiness and tackiness, upon and after application to skin, in comparison to a method wherein the phospholipid composition includes a refined phospholipid, e.g. refined lecithin or refined soy lecithin, and is otherwise identical.

Another unexpected result is that boron nitride, optionally in combination with a phospholipid, reduces the greasiness and tackiness of, for example, lubricants. Boron nitride had previously been shown to contribute lubricity to cosmetic powders and lipsticks for facial makeup use and to provide UV protection.

Another unexpected result is the extent to which the combination of zinc oxide and a phospholipid composition reduces the greasiness and tackiness of ointment compositions in accordance with the present invention. Zinc oxide USP and other regular forms of zinc oxide have previously been included in ointments that lack a phospholipid composition, but zinc oxide has had only a minimal effect in reducing greasiness and tackiness in such ointments. For example, classic zinc oxide ointment USP, which contains zinc oxide USP at 10 w/w %, exhibits and maintains a noticeable and undesirable degree of greasiness and tackiness after application to skin (as confirmed in Example 8, controls 2 and 3, below). Microfine zinc oxide, when used alone, may help reduce the shine of petrolatum, but it too has only a minimal effect on greasiness and residual tackiness when used alone, unless it is used in excessive amounts that may then become drying to the skin.

Another unexpected result associated with application of compositions in accordance with the present invention is the extent of the reduction in greasiness and tackiness associated with petrolatum present in the composition that results from the combination of: zinc oxide, preferably microfine zinc oxide; boron nitride, preferably alpha, hexagonal grade boron nitride; and a phospholipid composition, preferably a lecithin, and more preferably a natural soy lecithin. This reduction is further enhanced upon evaporation of a volatile oil, such as isohexadecane, cyclomethicone, cyclomethicone D4, isododecane, or other safe, volatile liquid oil, again after application.

In one embodiment, the present invention relates to a skin-protecting ointment composition that reduces greasiness based on including boron nitride in a concentration at or below 10 w/w %, optionally also including a phospholipid composition. This allows the use of substantial amounts of a normally greasy material, such as petrolatum, in combination with a wax, such as the saturated, high-molecular-weight paraffin hydrocarbon wax termed ozokerite, which is sometimes also termed mineral wax. The presence of the boron nitride, and optionally the phospholipid composition, greatly increases the cosmetic and therapeutic bioavailability and potency of the greasy material to the skin, in comparison to the use of emulsions, encapsulates, adsorbents, and absorbents. The delivery of the phospholipid composition optionally may be aided by dispersion in a volatile oil, such as isohexadecane, cyclomethicone, cyclomethicone D4, or isododecane.

In accordance with this embodiment, the skin-protecting ointment composition is preferably anhydrous, or free from water, and comprises: boron nitride at 0.5 to 15 w/w %, preferably at 1 to 8 w/w %, more preferably at 2 to 6 w/w %, the boron nitride preferably corresponding to crystalline, micronized, or microcrystallized boron nitride, more preferably corresponding to micronized or microcrystallized alpha hexagonal crystals of boron nitride; ozokerite at 5 to 40 w/w %, preferably at 10 to 35 w/w %, more preferably at 15 to 30 w/w %; a petrolatum, for example white petrolatum USP, at 25 to 65 w/w %, preferably at 35 to 55 w/w %, more preferably at 40 to 50 w/w %; cyclomethicone D4 at 10 to 50 w/w %, preferably at 20 to 40 w/w %, more preferably at 25 to 35 w/w %, and optionally a phospholipid composition at 0.1 to 5 w/w %, preferably at 1 to 3 w/w %, the phospholipid composition preferably comprising soy lecithin, more preferably non-deoiled soy lecithin. The boron nitride reduces the greasiness and tackiness of petrolatum and waxes, and the addition of a phospholipid, preferably a soy lecithin, more preferably a non-deoiled soy lecithin, substantially reduces the greasiness and tackiness further. For example, a skin-protecting ointment composition including boron nitride at 2 w/w % and a phospholipid at 2 w/w % exhibits reduced greasiness and tackiness. An ointment composition that includes boron nitride at 5 w/w % and that is otherwise identical exhibits a further enhancement of the reduction in greasiness and tackiness. And an ointment composition that includes a non-deoiled version of the phospholipid but that is otherwise identical (i.e. including boron nitride at 5 w/w %) exhibits a still further enhancement of the reduction in greasiness and tackiness.

In another embodiment, the present invention relates to a skin-protecting ointment composition that reduces greasiness based on including boron nitride in a concentration of less than 5 w/w % or based on including boron nitride and a phospholipid together at a combined concentration of less than 10 w/w %. This allows the use of up to 90 to 95 w/w % of a greasy material. The result is a substantial increase in the availability or bioavailability of the greasy material to skin or another substrate to which the ointment composition has been applied, in comparison to compositions including emulsions, encapsulates, adsorbents, or absorbents.

In accordance with this embodiment, the skin-protecting ointment composition is preferably anhydrous, or free from water, and comprises: boron nitride at 0.5 to 10.0 w/w %, the boron nitride preferably corresponding to crystalline, micronized, or microcrystallized boron nitride, more preferably corresponding to micronized or microcrystallized alpha hexagonal crystals of boron nitride; ozokerite at 5 to 20 w/w; petrolatum added qs as needed up to 100 w/w %, cyclomethicone, also added qs as needed up to 100 w/w %, and optionally a phospholipid composition at 0.0 to 5.0 w/w %, preferably at 1 to 3 w/w %, the phospholipid composition preferably comprising soy lecithin natural soy lecithin, or non-deoiled soy lecithin, more preferably natural soy lecithin or non-deoiled soy lecithin.

In another embodiment, the present invention relates to a skin-protecting ointment composition that reduces the greasiness and tackiness of the composition based on including zinc oxide, e.g. zinc oxide USP or other zinc oxide, and optionally and preferably, a phospholipid composition, and more preferably a natural or non-deoiled lecithin that still contains triglycerides. The reduction in greasiness and tackiness was further enhanced by use of microfine zinc oxide. The reduction in greasiness and tackiness was also further enhanced by optionally and preferably including a volatile oil, such as cyclomethicone D4 or isohexadecane. Specifically, upon evaporation of the volatile oil, the greasiness and tackiness of the compositions was reduced further. The reduction in greasiness and tackiness was even further enhanced by the combination of microfine grade zinc oxide and a non-deoiled phospholipid composition, such as non-deoiled lecithin or natural soy lecithin.

In accordance with this embodiment, the skin-protecting ointment composition is preferably anhydrous, or free from water, and comprises: zinc oxide at 0.1 to 20 w/w %, preferably at 0.5 to 10 w/w %, more preferably at 1 to 5 w/w %; petrolatum at 25 to 65 w/w %, preferably at 35 to 55 w/w %, more preferably at 40 to 50 w/w %; ozokerite at 1 to 40 w/w %, preferably at 10 to 30 w/w %, more preferably at 15 to 25 w/w %; isohexadecane, at 10 to 50 w/w %, preferably 20 to 40 w/w %, more preferably at 25 to 35 w/w %; and optionally and preferably a phospholipid composition at 0 to 10 w/w %, preferably at 0.5 to 5 w/w %, more preferably at 1 to 4 w/w %, the phospholipid preferably corresponding to soy lecithin, more preferably to non-deoiled soy lecithin.

Also in accordance with this embodiment, the skin-protecting composition comprises: zinc oxide at 0.2 to 20 w/w %, preferably at 0.8 to 15 w/w %, more preferably at 1 to 10 w/w %, more preferably at 2 to 6 w/w %; phospholipid composition at 0.1 to 10 w/w %, preferably 0.6 to 7 w/w %, more preferably 1 to 5 w/w %, more preferably 2 to 3 w/w %; petrolatum qs as needed to 100 w/w %; ozokerite wax qs as needed to 100 w/w %; and isohexadecane qs as needed to 100 w/w %.

In another embodiment, the present invention relates to a skin-protecting ointment composition that reduces the greasiness and tackiness of the composition based on including zinc oxide, preferably microfine zinc oxide, boron nitride, preferably alpha, hexagonal grade boron nitride, and a phospholipid composition, preferably a lecithin, and more preferably a natural soy lecithin.

In accordance with this embodiment, the skin-protecting ointment composition is preferably anhydrous, or free from water, and comprises: zinc oxide at 0.1 to 20 w/w %, preferably at 0.2 to 10 w/w %, more preferably at 0.3 to 5 w/w %; boron nitride at 0.1 to 5.0 w/w %, preferably at 1.0 to 4.0 w/w %, more preferably at 1.5 to 3.0 w/w %; petrolatum at 25 to 65 w/w %, preferably at 35 to 55 w/w %, and more preferably at 40 to 50 w/w %; ozokerite wax at 1 to 40 w/w %, preferably at 10 to 30 w/w %, more preferably at 15 to 25 w/w %; isohexadecane at 10 to 50 w/w %, preferably at 20 to 40 w/w %, more preferably at 25 to 35 w/w %; and optionally soy lecithin at 0 to 10 w/w %, preferably at 0.5 to 5.0 w/w %, more preferably at 1.0 to 4.0 w/w %, the soy lecithin preferably corresponding to natural soy lecithin or non-deoiled soy lecithin.

Also in accordance with this embodiment, the skin-protecting ointment composition is preferably anhydrous, or free from water, and comprises: zinc oxide at 0.2 to 20 w/w %, preferably at 0.3 to 10 w/w %, more preferably at 0.4 to 5 w/w %; boron nitride at 0.2 to 20.0 w/w %, preferably at 0.4 to 10.0 w/w %, more preferably at 0.6 to 5.0 w/w %; soy lecithin at 0.1 to 10 w/w %, preferably at 0.5 to 5.0 w/w %, more preferably at 1.0 to 4.0 w/w %, the soy lecithin preferably corresponding to natural soy lecithin or non-deoiled soy lecithin; petrolatum added qs as needed to 100 w/w %; ozokerite added qs as needed to 100 w/w %; and isohexadecane added qs as needed to 100 w/w %.

In another embodiment, the present invention relates to skin-protecting compositions that are anhydrous.

In accordance with another aspect of the present invention, a method of making a skin-protecting ointment composition comprises: combining a greasy material and a safe and minimally absorbed solid, preferably by first melting the greasy material and then adding the safe and minimally absorbed solid; mixing the greasy material and the safe and minimally absorbed solid, preferably at 65° to 85° C., more preferably at 70° to 80° C., more preferably at 75° C.; adding a phospholipid composition dissolved in a volatile oil, the phospholipid composition preferably comprising a natural phospholipid, a non-deoiled phospholipid, a natural lecithin, a non-deoiled lecithin, a natural soy lecithin, or a non-deoiled soy lecithin, the solution of the phospholipid composition in the volatile oil being at 15° to 30° C., preferably at 18° to 25° C., more preferably at 20° to 23° C., just prior to addition; and cooling the resulting composition to impede oxidation of the phospholipid composition mixed therein, preferably by rapidly cooling the resulting composition to 20° to 40° C., preferably 25° to 35° C., more preferably to 30° C.; said ointment composition exhibiting reduced greasiness and tackiness relative to an otherwise identical composition lacking the safe and minimally absorbed solid and the phospholipid composition.

In accordance with another aspect of the present invention, a method of reducing the greasiness and tackiness of a skin-protecting ointment composition comprises the steps of combining a greasy material, a safe and minimally absorbed solid, and a non-deoiled phospholipid composition that is dissolved in a volatile oil to form the skin-protecting ointment composition, said skin-protecting ointment composition exhibiting reduced greasiness and tackiness relative to an otherwise identical composition lacking the safe and minimally absorbed solid and the non-deoiled phospholipid composition. In accordance with this embodiment, the greasy material preferably comprises: a lipid thickener, preferably at 1 to 40 w/w %, more preferably at 10 to 30 w/w %, more preferably at 15 to 25 w/w %; an ointment-like material, preferably at 25 to 65 w/w %, more preferably at 35 to 55 w/w %, more preferably at 40 to 50 w/w %; and a volatile oil, preferably at 10 to 50 w/w %, more preferably at 20 to 40 w/w %, more preferably at 25 to 35 w/w %; the lipid thickener preferably being selected from the group consisting of wax, ozokerite wax (i.e. ozokerite), beeswax, other natural and synthetic waxes, and lipid miscible thickener; the ointment-like composition preferably being selected from the group consisting of petrolatum, lanolin, and natural and synthetic lipids, including high molecular weight glycerides and polyethylene glycols and the like; and the volatile oil preferably being selected from the group consisting of isohexadecane, cyclomethicone, cyclomethicone D4, isododecane, and safe, volatile liquid oil. In accordance with this embodiment, the safe and minimally absorbed solid preferably is selected from the group consisting of boron nitride, boron nitride in a crystalline form, boron nitride in the form of micronized or microcrystallized alpha hexagonal crystals, zinc oxide, titanium dioxide, polytetrafluoroethylene, talcum, and pigments, and is present at 0.1 to 20 w/w %, preferably at 0.2 to 10 w/w %, more preferably at 0.3 to 5 w/w %. In accordance with this embodiment, the non-deoiled phospholipid composition preferably is selected from the group consisting of a natural phospholipid, a non-deoiled phospholipid, a natural lecithin, a non-deoiled lecithin, a natural soy lecithin, and a non-deoiled soy lecithin, and is present at 0.1 to 10 w/w %, preferably at 0.5 to 5.0 w/w %, more preferably at 1.0 to 4.0 w/w %. In accordance with this embodiment, the greasy material and the safe and minimally absorbed solid preferably may be combined by mixing the greasy material and the safe and minimally absorbed solid, preferably at 65° to 85° C., more preferably at 70° to 80° C., more preferably at 75° C. In accordance with this embodiment, the non-deoiled phospholipid composition that is dissolved in the volatile oil is preferably at 15° to 30° C., more preferably at 18° to 25° C., and more preferably at 20° to 23° C., just prior to addition to the greasy material and the safe and minimally absorbed solid. Also in accordance with this embodiment, upon addition of the non-deoiled phospholipid composition, oxidation of the non-deoiled phospholipid composition may be impeded, preferably by rapidly cooling the resulting composition to 20° to 40° C., preferably 25° to 35° C., more preferably to 30° C.

Example 1

Skin-protecting ointment compositions in accordance with the present invention were produced according to the following formulations:

| Ingredient (Supplier/Product identification) | Composition 342-E1 (w/w %) | Composition 342-E2 (w/w %) |
|---|---|---|
| Petrolatum (Merkur 773) | 45.0 | 45.0 |
| Ozokerite wax (TECe-Ozokerit N 502) | 20.0 | 20.0 |
| Zinc oxide (Horsehead) | 0.50 | 0.50 |
| Boron nitride (Saint Gobain PUHP #3005 | 2.00 | 3.00 |
| Soy lecithin (ADM ADLEC COD, E 322) | 2.00 | 2.00 |
| Isododecane | 30.50 | 29.50 |

Note that cyclomethicone, cyclomethicone D4, or isohexadecane can be used in place of isododecane in compositions 342-E1 and 342-E2 to yield a slightly heavier, thicker product.

Compositions 342-E1 and 342-E2 were manufactured according to the following procedure: Heat the petrolatum, ozokerite, zinc oxide, and boron nitride while stirring to 75° C. When a suspension has been obtained, stop heating. Add soy lecithin, pre-dissolved in isododecane (or cyclomethicone or cyclomethicone D4), the soy lecithin solution being at room temperature. With continuous stirring, add the soy lecithin dissolved in the isododecane, and cool the mixture to 35° C. If possible, keep the kettle headspace covered with nitrogen, as this will prevent brownish discoloration and development of an off-smell by lecithin. Finally, package the resulting composition at the lowest practical pouring temperature.

Suppliers for ingredients of the compositions include the following:

| Ingredient | Supplier | Location |
|---|---|---|
| Petrolatum | Merkur | Germany |
| Ozokerite | Tromm, Koln | Cologne, Germany |
| Boron nitride | Saint Gobain | Amherst, New York |
| Zinc oxide | Horsehead Corp. | Pittsburgh, Pennsylvania |
| Soy lecithin | ADM | U.S. |
| Isododecane | U.S. supplier | U.S. |
| Cyclomethicone | U.S. supplier | U.S. |

Example 2

Skin-protecting ointment compositions were produced, essentially as described in Example 1, according to the following formulations:

| Ingredient | Composition 345-A2 (w/w %) | Composition 345-A3 (w/w %) |
|---|---|---|
| Petrolatum, Merkur 773 | 45 | 45 |
| Ozokerite ,Tromm | 20 | 20 |
| Soy lecithin, non-deoiled | 2 | 2 |
| Boron nitride, PUHP 30003, St. Gobain | 1.5 | 2 |
| Zinc oxide, BASF | 0.5 | 0.5 |
| Isododecane | 31 | 30.5 |

Compositions 345-A2 and 345-A3 were then tested for tackiness according to the following procedure: Approximately 60 to 72 mg of composition was placed on the tip of the middle finger and gently rubbed into an area of approximately 15 to 18 $cm^2$ on the forearm, resulting in application of approximately 4 mg composition per $cm^2$ of skin, and rubbed in for 15 seconds ("area A"). The treatment was immediately repeated in a comparable adjacent area of skin ("area B"). The initial value (i.e. at time=0 min) of tackiness was determined by pressing an index finger on area A and then estimating tackiness on the following scale: 0=none; 1=light; 2=light to moderate; 3=moderate; 4=moderate to substantial; and 5=substantial. After 15 minutes, the test was repeated on area B. Further tests were run on separate areas of skin. This test could be repeated on the same area of skin after 24 or more hours.

Compositions 345-A2 and 345-A3 show practically no tackiness within fifteen minutes after application of a typical amount. Both of the compositions are anhydrous and both may readily be applied to relatively large areas of skin due to the ointment properties, in contrast to, for example, stick cosmetics.

Example 3

Skin-protecting ointment compositions were produced, essentially as described in Example 1, according to the following formulations:

| Ingredient | Example 3-A (w/w %) | Example 3-B (w/w %) | Example 3-C (w/w %) |
|---|---|---|---|
| Boron nitride, hexagonal | 5.0 | 2.5 | 5.0 |
| Soy lecithin | 0 | 2.5 | 2.0 |
| Ozokerite | 20.0 | 20.0 | 20.0 |
| Petrolatum | 47.0 | 46.0 | 45.0 |
| Cyclomethicone D4 | 28.0 | 29.0 | 28.0 |

Example 4

A skin-protecting ointment composition was produced, essentially as described in Example 1, according to the following formulation:

| Ingredient | Example 4-A (w/w %) |
|---|---|
| Boron nitride, hexagonal | 5.0 |
| Phospholipid | 2.0 |
| Ozokerite | 20.0 |
| Petrolatum | 45.0 |
| Cyclomethicone D4 | 28.0 |

Example 5

Skin-protecting ointment compositions were produced, essentially as described in Example 1, according to the following formulations:

| Ingredient | Example 5-A (w/w %) | Example 5-B (w/w %) | Example 5-C (w/w %) |
|---|---|---|---|
| Zinc oxide | 2.0 | 3.0 | 5.0 |
| Soy lecithin | 2.0 | 2.0 | 3.0 |
| Petrolatum | 45.0 | 44.0 | 42.0 |
| Ozokerite | 20.0 | 20.0 | 18.5 |
| Isohexadecane | 31.0 | 31.0 | 31.5 |

Example 6

Skin-protecting ointment compositions were produced, essentially as described in Example 1, according to the following formulations:

| Ingredient | Example 6-A (w/w %) | Example 6-B (w/w %) | Example 6-C (w/w %) |
|---|---|---|---|
| Zinc oxide | 0.5 | 1.5 | 3.0 |
| Boron nitride | 3.0 | 2.0 | 1.5 |
| Soy lecithin | 2.0 | 2.0 | 3.0 |
| Petrolatum | 44.5 | 44.0 | 42.0 |
| Ozokerite | 20.0 | 20.0 | 19.0 |
| Isohexadecane | 30.0 | 30.5 | 31.5 |

Example 7

Skin-protecting ointment compositions were produced, essentially as described in Example 1, according to the following formulations:

| Ingredient | Example 7-A (w/w %) | Example 7-B (w/w %) | Example 7-C (w/w %) | Example 7-D (w/w %) |
|---|---|---|---|---|
| Zinc oxide | 0.5 | 1.0 | 1.5 | 2.0 |
| Boron nitride | 1.5 | 1.0 | 0.5 | 2.0 |
| Soy lecithin | 2.0 | 2.0 | 2.0 | 3.0 |
| Petrolatum | 45.0 | 45.0 | 45.0 | 43.0 |
| Ozokerite | 20.0 | 20.0 | 20.0 | 19.5 |
| Isohexadecane | 31.0 | 31.0 | 31.0 | 30.5 |

Example 8

Skin-protecting ointment compositions, corresponding to controls 1 to 3 (C1 to C3) and treatments 1 to 10 (T1 to T10), were produced, essentially as described in Example 1, according to the following formulations:

| Ingredients | C1 | C2 | C3 | T1 | T2 | T3 | T4 | T5 | T6 | T7 | T8 | T9 | T10 |
|---|---|---|---|---|---|---|---|---|---|---|---|---|---|
| Boron nitride | 0 | 0 | 0 | 0 | 0 | 0 | 1.5 | 2 | 2 | 3 | 2 | 2 | 3 |
| Zinc oxide | 0 | 10 | 10 | 10 | 10 | 10 | 0.5 | 0.5 | 0 | 0 | 2 | 2 | 3 |
| Non-deioled soy lecithin | 0 | 0 | 0 | 2 | 2 | 2 | 2 | 2 | 2 | 2 | 2 | 2 | 2 |
| Ozokerite | 0 | 0 | 20 | 20 | 20 | 20 | 20 | 20 | 20 | 20 | 20 | 20 | 18 |
| Petrolatum | 100 | 90 | 70 | 68 | 38 | 38 | 45 | 45 | 38 | 38 | 37 | 37 | 36 |
| Isohexadecane | 0 | 0 | 0 | 0 | 30 | 0 | 31 | 30.5 | 0 | 0 | 37 | 0 | 0 |
| Cyclomethicone | 0 | 0 | 0 | 0 | 0 | 30 | 0 | 0 | 38 | 37 | 0 | 37 | 38 |

The compositions were then tested for tackiness, according to the procedure described above in Example 2. The results of the tests for tackiness were as follows:

| Estimated tackiness | C1 | C2 | C3 | T1 | T2 | T3 | T4 | T5 | T6 | T7 | T8 | T9 | T10 |
|---|---|---|---|---|---|---|---|---|---|---|---|---|---|
| 0 minutes | 5 | 5 | 4.5 | 4.5 | 3.5 | 3 | 3 | 2.5 | 2.5 | 2 | 1.5 | 1.5 | 1 |
| 15 minutes | 5 | 5 | 4.5 | 3.5 | 2.5 | 2.5 | 2 | 1.5 | 2 | 1 | 0.5 | 0.5 | 0-0.5 |

The invention has been described with reference to the example embodiments described above. Modifications and alterations will occur to others upon a reading and understanding of this specification. Example embodiments incorporating one or more aspects of the invention are intended to include all such modifications and alterations insofar as they come within the scope of the appended claims.

What is claimed is:

1. A skin-protecting ointment composition comprising:
   a safe and minimally absorbed solid, selected from the group consisting of boron nitride, boron nitride in a crystalline form, and boron nitride in the form of micronized or microcrystallized alpha hexagonal crystals, at 1.5 to 4.0 w/w %;
   a lipid thickener, selected from the group consisting of wax, ozokerite wax, beeswax, natural and synthetic waxes, and lipid miscible thickener, at 5 to 40 w/w %;
   petrolatum at 35 to 50 w/w %; and
   a volatile oil at 20 to 40 w/w %;
   said ointment composition exhibiting reduced greasiness and tackiness relative to an otherwise identical composition lacking the safe and minimally absorbed solid.

2. The ointment composition of claim 1, said volatile oil being selected from the group consisting of isohexadecane, cyclomethicone, cyclomethicone D4, isododecane, and safe, volatile liquid oil.

3. The ointment composition of claim 1, further comprising a phospholipid composition selected from the group consisting of a phospholipid, a refined phospholipid, a natural phospholipid, a non-deoiled phospholipid, a lecithin, a refined lecithin, a natural lecithin, a non-deoiled lecithin, a soy lecithin, a refined soy lecithin, a natural soy lecithin, a non-deoiled soy lecithin, and a modified lecithin.

4. The ointment composition of claim 1, further comprising a phospholipid composition selected from the group consisting of a natural lecithin, a non-deoiled lecithin, a natural soy lecithin, and a non-deoiled soy lecithin, said phospholipid composition at 0.1 to 10 w/w %.

5. The ointment composition of claim 1, said ointment composition being anhydrous; said safe and minimally absorbed solid comprising boron nitride in the form of micronized or microcrystallized alpha hexagonal crystals; said lipid thickener comprising ozokerite wax at 5 to 40 w/w %; and said volatile oil comprising cyclomethicone D4 at 20 to 40 w/w %.

6. The ointment composition of claim 5, further comprising a phospholipid composition selected from the group consisting of a natural lecithin, a non-deoiled lecithin, a natural soy lecithin, and a non-deoiled soy lecithin, said phospholipid composition at 0.1 to 10 w/w %.

7. The ointment composition of claim 1, said ointment composition further comprising zinc oxide at 0.3 to 10 w/w %.

8. The ointment composition of claim 7, further comprising a phospholipid composition selected from the group consisting of a natural lecithin, a non-deoiled lecithin, a natural soy lecithin, and a non-deoiled soy lecithin, said phospholipid composition at 0.1 to 10 w/w %.

9. The ointment composition of claim 1, said ointment composition being anhydrous; said ozokerite wax present at 5 to 40 w/w %; and said volatile oil selected from the group consisting of isohexadecane and isododecane and present at 20 to 40 w/w %.

10. The ointment composition of claim 9, further comprising a phospholipid composition selected from the group consisting of a natural lecithin, a non-deoiled lecithin, a natural soy lecithin, and a non-deoiled soy lecithin, said phospholipid composition at 0.1 to 10 w/w %.

11. A method of protecting skin, comprising the steps of applying the skin-protecting ointment composition of claim 1 to skin and rubbing the composition into the skin.

12. A skin-protecting ointment composition comprising boron nitride at 1.5 to 4.0 w/w %, a lipid thickener at 5 to 40 w/w %, petrolatum at 35 to 50 w/w %, and a volatile oil at 20 to 40 w/w %, said ointment composition exhibiting reduced greasiness and tackiness relative to an otherwise identical composition lacking the boron nitride.

13. The ointment composition of claim 12, said boron nitride being in the form of micronized or microcrystallized alpha hexagonal crystals; said lipid thickener being selected from the group consisting of wax, ozokerite wax, beeswax, natural and synthetic waxes, and lipid miscible thickeners; and said volatile oil being selected from the group consisting of isohexadecane, cyclomethicone, cyclomethicone D4, isododecane, and safe, volatile liquid oil.

14. The ointment composition of claim 13, said ointment composition being anhydrous; said lipid thickener comprising ozokerite wax at 5 to 40 w/w %; and said volatile oil comprising cyclomethicone D4 at 20 to 40 w/w %.

15. The ointment composition of claim 1, said safe and minimally absorbed solid at 1.5 to 3.0 w/w %.

16. The ointment composition of claim 1, said petrolatum at 40 to 50 w/w %.

17. The ointment composition of claim 16, said safe and minimally absorbed solid at 1.5 to 3.0 w/w %.

18. The ointment composition of claim 12, said boron nitride at 1.5 to 3.0 w/w %.

19. The ointment composition of claim 12, said petrolatum at 40 to 50 w/w %.

20. The ointment composition of claim 19, said boron nitride at 1.5 to 3.0 w/w %.

* * * * *